(12) United States Patent
Alpan et al.

(10) Patent No.: US 10,751,328 B2
(45) Date of Patent: Aug. 25, 2020

(54) THERAPY FOR CHRONIC IDIOPATHIC URTICARIA, ANAPHYLAXIS AND ANGIOEDEMA

(71) Applicants: Oral Alpan, Fairfax, VA (US); Benjamin I. Enav, Burke, VA (US)

(72) Inventors: Oral Alpan, Fairfax, VA (US); Benjamin I. Enav, Burke, VA (US)

(*) Notice: Subject to any disclaimer, the term of this patent is extended or adjusted under 35 U.S.C. 154(b) by 0 days.

(21) Appl. No.: 15/031,991

(22) PCT Filed: Oct. 27, 2014

(86) PCT No.: PCT/US2014/062389
§ 371 (c)(1),
(2) Date: Apr. 25, 2016

(87) PCT Pub. No.: WO2015/061777
PCT Pub. Date: Apr. 30, 2015

(65) Prior Publication Data
US 2016/0271112 A1 Sep. 22, 2016

Related U.S. Application Data

(60) Provisional application No. 61/895,890, filed on Oct. 25, 2013.

(51) Int. Cl.
*A61K 31/429* (2006.01)
*A61K 45/06* (2006.01)
*A61K 31/428* (2006.01)
*A61K 9/00* (2006.01)

(52) U.S. Cl.
CPC .......... *A61K 31/429* (2013.01); *A61K 9/0053* (2013.01); *A61K 31/428* (2013.01); *A61K 45/06* (2013.01)

(58) Field of Classification Search
CPC .................................................. A61K 31/429
USPC ........................................................ 514/367
See application file for complete search history.

(56) References Cited

U.S. PATENT DOCUMENTS

| | | | |
|---|---|---|---|
| 6,653,325 B2 * | 11/2003 | Svensson | A61K 31/445 514/317 |
| 8,518,926 B2 | 8/2013 | Bozik et al. | |
| 9,891,213 B2 * | 2/2018 | Gernez | G01N 33/5094 |
| 2007/0259930 A1 | 11/2007 | Bozik et al. | |
| 2008/0200505 A1 * | 8/2008 | Perry | C07D 211/46 514/316 |
| 2013/0158017 A1 | 6/2013 | Zhu et al. | |
| 2016/0193186 A1 * | 7/2016 | Bozik | A61K 31/428 514/367 |

FOREIGN PATENT DOCUMENTS

| WO | WO 2011/150221 A2 | 12/2011 |
|---|---|---|
| WO | WO 2015/023790 A1 | 2/2015 |

OTHER PUBLICATIONS

Yasnowsky et al. J Allergy Clin Immunol 2006;117:1430-4.*
Chinuki, J Allergy Clin Immunol, 1304-1406, 2012.*
Simons, Annals of Allergy, Asthma Immunology, 104(5):405-412.*
Ansel, Pharmaceutical Dosage Forms and Drug Delivery Systems, 1999.*
Marriott, Pharmaceutical Compound and Dispensing, Second Edition, 2010, 1-288.*
International Search Report dated Feb. 2, 2015 in International Application No. PCT/US2014/062389 (1 page).
International Preliminary Report dated May 6, 2016 in International Application No. PCT/US2014/062389 (8 pages).
U.S. Appl. No. 61/865,583, of Bozik, filed Aug. 13, 2013 (84 pages).
U.S. Appl. No. 61/987,117, of Bozik et al, filed May 14, 2014 (87 pages).
Knopp Biosciences, "Dexpramipexole Decreases Blood Ensinophils: Results of Two Clinical Trials in Patients with Amyotrophic Lateral Sclerosis," by Michael E. Bozik, Thomas Petzinger, Jr., James L. Mather, Gregory T. Hebrank, Steven I. Dworetzky, Ian J. Reynolds, Mary Sullivan, Wildon R. Farwell, Knopp Biosciences, Teva Pharmaceuticals, and Biogen Idec, undated (14 pages) Jul. 2013.
Expression of CD203c and CD63 in Human Basophils: Relationship to Differential Regulation of Piecemeal and Anaphylactic Degranulation Processes, by Donald MacGlashan, Jr., Sep. 2010, Clinical & Experimental Allergy, vol. 40, Issue 9, pp. 1365-1377 (20 pages).

\* cited by examiner

*Primary Examiner* — Nizal S Chandrakumar
(74) *Attorney, Agent, or Firm* — Nixon & Vanderhye P.C.

(57) ABSTRACT

Methods for treating or relieving at least one symptom of urticarial disorders including chronic idiopathic urticaria, angioedema, and anaphylaxis, or a combination of these disorders in a mammal, including humans. The method comprises administering to the mammal a therapeutically effective amount of pramipexole, dexpramipexole or pharmaceutically acceptable salts thereof.

16 Claims, 5 Drawing Sheets

THERAPY FOR CHRONIC IDIOPATHIC URTICARIA, ANAPHYLAXIS AND ANGIOEDEMA

RELATED APPLICATION

This application is the U.S. national phase of International Application No. PCT/US2014/062389 filed Oct. 17, 2014 which designated the U.S. and claims priority to 61/895,890 filed Oct. 25, 2013, the entire contents of each of which are hereby incorporated by reference.

TECHNICAL BACKGROUND

This invention relates to methods for treating urticarial disorders, angioedema and anaphylaxis by administering pramipexole, dexpramipexole or related compounds.

BACKGROUND OF THE INVENTION

Urticaria

Urticaria, commonly referred to as hives, is a kind of skin rash notable for pale red, raised, itchy bumps. Burning or stinging sensation may also be present. Hives are frequently caused by allergic reactions; however, there are many non-allergic causes. Most cases of hives lasting less than six weeks (acute urticaria) are the result of an allergic trigger. Chronic urticaria (hives lasting longer than six weeks) is rarely due to an allergy.

The majority of chronic hives cases have an unknown (idiopathic) cause. In perhaps as many as 30-40% of patients with chronic idiopathic urticaria, it is caused by an autoimmune reaction. Acute viral infection is another common cause of acute urticaria (viral exanthem). Less common causes of hives include friction, pressure, temperature extremes, exercise, and sunlight.

Urticaria is one of the most common allergic dermatological conditions. The disease appears as a vascular reaction, characterized by red, raised, itchy circumscribed areas of dermal edema. The disease is classed as acute or chronic based on the persistence of the wheal (raised areas of skin) and whether they do or do not spontaneously resolve. Deeper swellings of the skin (angiodema discussed below) can also occur which are painful rather than itchy. Urticaria and angiodema may co-exist but either may occur alone. Chronic urticaria is a distressing condition with a very significant impact on the quality of life of the patient. The pathophysiology of urticaria is not well understood, however, an important factor in many patients in progression of the disease is the release of histamine from skin mast cells.

The physiological effects of histamine are classically mediated by four receptor subtypes, termed $H_1$, $H_2$, $H_3$ and $H_4$. The erythema, wheal formation and itching associated with urticaria are due to activation of $H_1$ receptors. Histamine $H_2$ receptors can also play a role in the wheal response produced by localized histamine since it has been demonstrated that $H_2$ antagonists attenuate the immediate vascular responses of intradermal (i.d.) injections of histamine. Combination treatment with a $H_1$ and $H_2$ antagonist is more effective in reducing the urticaria, itching and wheal and flare responses than treatment with either an $H_1$ or $H_2$ antagonist alone although the synergistic effect of combined $H_1$ and $H_2$ antagonist treatment for urticaria remains controversial since some investigators have not been able to demonstrate an improvement in chronic idiopathic urticaria with dual $H_1$ and $H_2$ antagonist treatment (see, for example, Commens C A. & Greaves M. W., Brit. J. Dermatol., 1978, 99, 675-679; Cook L. J. & Shuster S. H., Acta Dermato-Venereologica (Stockh), 63, 265-267).

Glucocorticosteroids, a potent therapy for most allergic disorders, do not affect mediator secretion from mast cells, but have been shown to inhibit histamine release from basophils (Schleimer, et al., J. Immunol., 143:1310; 1989). Thus, the inhibition of basophil mediator release may be one of the mechanisms by which glucocorticosteroids abolish the late phase allergic reaction and control the symptoms of chronic asthma and allergy. Basophils have also been implicated a number of other allergic disorders, such as food allergy and atopic dermatitis (May, J. Allergy Clin. Immunol., 58:432-437; 1976 and Sampson, et al., New Engl. J. Med., 321:228; 1989). Unfortunately, despite the evidence linking mast cells and basophils to these and other disease states, the precise pathogenesis of mast cell and basophil dependent disorders, including allergic disease, is not fully understood. For example, it is known that mast cells and basophils are stimulated to release histamine, leukotrienes, and other inflammatory mediators by the bridging of cell surface-bound IgE antibodies by appropriate allergens.

Moreover, although mast cells are believed to play a role in various other diseases such as inflammatory bowel disease, rheumatoid arthritis, pulmonary fibrosis, and sarcoidosis, in the majority of these diseases, IgE antibody cannot be found. Therefore, it appears that other mechanisms of allergic mediator release play a critical role in pathogenesis of allergic diseases and other disorders mentioned above in which basophils and mast cells have been implicated. Elucidation of such mechanisms has been and remains the goal of many skilled medical scientists.

One of the most exciting developments in this area was the discovery of histamine releasing activity (HRA), cytokines designated herein as histamine releasing factor(s) (HRF). Thueson, et al., (J. Immunol., 123:626, 1979; J. Immunol., 123:633, 1979) and Lett-Brown, et al., (Cell Immunol., 87:434, 1984; Cell Immunol., 87:445, 1984) first reported that antigen or mitogen stimulated human mononuclear cells secrete a proteinaceous factor that induces release of histamine from basophils and mast cells. Other laboratories then confirmed the synthesis of HRF by mononuclear cells. It has now been shown that HRF is also synthesized by B-lymphocytes and T-lymphocytes, alveolar macrophages, platelets, neutrophils, and blood monocytes cultured in vitro. The wide variety of cell types reported to secrete HRF suggests that it has considerable biologic importance. In addition to mediating histamine release, HRF has been shown to induce secretion of leukotrienes and to be chemotactic for basophils and monocytes. For a review, see Grant, et al., Fed. Proc, 45:2653, 1986, J. Allergy Clin. Immunol., 77:407, 1986, and Ala, Insights in Allergy, Vol. 2, no. 6, 1987, C V Mosby, St. Louis, and Grant, et al., J. Allergy Clin. Immunol. 88:683-693 (1991), all incorporated herein by reference.

"Chronic idiopathic urticaria" as used herein, is itchy hives that last for at least 6 weeks, and that have no apparent external trigger. The condition generally has a prolonged duration of 1 to 5 years (persisting for >5 years in 20 percent of patients) and has a detrimental effect on patients' emotional and physical health-related quality of life. The impairment accompanying this disorder has been likened to that seen in patients with ischemic heart disease, with patients feeling a similar lack of energy, social isolation, and emotional upset as those with heart disease.

Nonsedating H1-antihistamines are the current mainstay for initial treatment of urticaria and are the only agents licensed for use in patients with chronic idiopathic urticaria.

However, a majority of patients do not have a response to H1-antihistamines, even when the drugs are administered at three to four times their licensed dose.

Treatment options for urticaria patients who do not have a response to H1-antihistamines include the use of H2-antihistamines, leukotriene-receptor antagonists, systemic glucocorticoids, cyclosporine, hydroxychloroquine, dapsone, methotrexate, sulfasalazine, and intravenous immune globulin. None of these agents have yet received regulatory approval for the treatment of chronic idiopathic urticaria. In addition, the data supporting the use of these drugs are limited, and long-term use of some of the agents can be associated with substantial side effects. Histamine release from cutaneous mast cells has long been associated with the pathogenesis of urticaria. Several proof-of concept studies showed that omalizumab may be effective in patients with chronic idiopathic urticaria who remained symptomatic despite antihistamine treatment through its reduction of FcεRI function in basophils and mast cells. Subsequent data from two phase 2, randomized, placebo-controlled multicenter studies involving a total of 139 patients corroborated these early findings, demonstrating that omalizumab, which has a known safety profile, has beneficial effects on symptoms in patients with chronic idiopathic urticaria who remain symptomatic despite the use of approved doses of H1-antihistamines. (Maurer M, Rosén K, Hsieh H J, Saini S, Grattan C, Gimenéz-Arnau A, Agarwal S, Doyle R, Canvin J, Kaplan A, Casale T. N Engl J Med. 2013 Mar. 7; 368(10):924-35.)

The activated mast cells and basophils in CIU will express the CD63, a member of the transmembrane-4 superfamily, which is a mast cell and basophils activation marker as a result of the fusion between intracytoplasmic granules and the plasma membrane. Another marker on activated mast cells and basophils, which is more specific, is CD203c (ectonucleotid pyrophosphatase/phosphodiesterase) is an ectoenzyme expressed only on resting and activated basophils, mast cells in response to cross-linking of the FcεRIα receptors and their CD34+ progenitor cells in peripheral blood. Histamine is certainly the main mediator involved in CAU, de novo (newly synthesises) of leukotriene C4 (LTC4) also induced. The LTC4 is about 1,000 times more potent than histamine in causing wheal and flare reaction. There is little evidence that platelet-activating factor, cytokines, and chemokines released by activated mast cells, are involved in the pathogenesis of urticarial lesions.

Angioedema

Angioedema refers to abrupt non-pitting swelling of the skin, mucous membranes, or both, including the upper respiratory and gastrointestinal tracts, which typically lasts from many hours to 3 days. The involved tissues then return to normal. Sites of predilection include the face, hands, feet, and genitalia. Lip and eye (periorbital) swelling is the most common. Swelling of the tongue, pharynx, and larynx is particularly problematic. Fatalities can occur because of laryngeal edema, but pharyngeal edema and tongue swelling can be similarly disastrous if they are massive.

Angioedema is caused by a rapid increase in permeability of sub mucosal or subcutaneous capillaries and post-capillary venules with localized plasma extravasation. Most causes of angioedema are dependent upon the release of either histamine or bradykinin; other vasoactive substances may be contributory. However, no firm data are available with regard to prostaglandins, leukotrienes, or enzymes such as tryptase, or cytokines, or chemokines. Leukotrienes are suspect when angioedema occurs with cyclooxygenase 1 (COX-1) inhibitors.

Bradykinin is the mediator of angioedema associated with angiotensin-converting enzyme (ACE) inhibitors that prevent bradykinin destruction so that levels rise. The source of bradykinin formation can either be the plasma or tissue bradykinin-forming pathways. C1 inhibitor (INH) deficiency, either hereditary or acquired, leads to overproduction of bradykinin caused by absent inhibition of the enzymes kallikrein and activated factor XII.

Angioedema is a swelling with the overlying skin (or mucous membrane) either normal or erythematous. It typically does not last more than 72 hours, and the site of involvement returns to normal. It may then recur at the same site or other locations. It may or may not be pruritic, but when itch is present, it is rarely intense. A burning dysesthesia may be present. Tingling of the area and a slightly numb feeling may precede the onset of obvious swelling. An urticarial lesion or hive presents with a clearly circumscribed border separating normal from involved skin, there is prominent erythema that blanches with pressure, it is typically very pruritic, and although palpable, does not form a lump as does angioedema. Whereas most urticarial lesions last 8 to 36 hours (except for fleeting hives of some physical urticarias), angioedema, if severe, lasts longer.

Urticaria and angioedema are often seen together in allergic reactions to foods and drugs including anaphylaxis, both may be present in the physically induced urticarias (although hives predominate), or in patients with chronic idiopathic or autoimmune urticaria/angioedema.

Anaphylaxis

While anaphylaxis may result from exposure to almost any foreign substance, most episodes have an identifiable trigger. Medications may trigger anaphylaxis either via IgE interactions or by direct mast cell stimulation. When medications are suspected of triggering anaphylaxis, a detailed history is invaluable. The timing of the reaction with ingestion or injection of the suspected agent as well as prior exposure can help identify the offending agent. Laboratory IgE evaluations for most medications are unavailable. Skin testing to penicillin is once again available and its judicious use may aid diagnosis. Given lack of exposure and level of patient impairment, anaphylaxis during surgery may be identified only after cardiac symptoms arise. Anesthetic-induced anaphylaxis occurs between 1:3500 and 1:20,000 cases with mortality in up to 4% of cases. Envenomation continues to be a cause of rapid and fatal anaphylaxis. Most fatal events occur on first sting exposure, and up to 96% of fatal reactions begin within 30 minutes of the sting. Exercise has been demonstrated to induce anaphylaxis, although the pathogenesis of exercise-induced anaphylaxis (EIA) is not known. At least one study suggests that up to 50% of episodes of EIA are related to food ingestion prior to the exercise. In children, foods are the most common trigger of anaphylaxis requiring emergency services. While most food-induced reactions are not fatal, the majority of fatal reactions occur in persons with a previous history of food-induced anaphylaxis. Idiopathic anaphylaxis remains a diagnosis of exclusion. As with other forms of anaphylaxis, the true incidence of idiopathic anaphylaxis is unknown, but some suggest that 6% to 31% of anaphylaxis cases remain without an identified trigger.

In some cases, the clinical diagnosis of anaphylaxis can be confirmed with laboratory testing. Serum tryptase and plasma histamine levels may suggest anaphylaxis while neither test is specific to anaphylaxis. Additionally, sample collection and handling may affect the validity of the results. Comparing serial measurements of total tryptase to the patient baseline level may prove more helpful in diagnosing anaphylaxis than reliance on a single acute measurement. As indicated above, the history of the event holds a central role in the identification of possible triggers. The history should include at minimum the suspected trigger with dose size, the timing and route of exposure, the timing, sequence, and duration of symptoms, the timing and response to interventions and associated events (e.g. exercise or co-administration of medications). If possible, medical records of the acute event should be evaluated to confirm the history. The careful history can then guide additional testing in order to confirm the presumptive trigger. Skin testing with commercial extracts to foods or venom should be performed with validated instruments and techniques. Results should be recorded so that the method of testing and source of the test sample are easily identifiable. Skin testing may be unreliable in the 3 to 4 weeks immediately following anaphylaxis, and negative results should be repeated. While both skin prick and intradermal testing is often required for the evaluation of venom-induced anaphylaxis, intradermal testing should be avoided in suspected food allergy because they lack specificity (high rate of false-positive tests) and the potential for inducing anaphylaxis during testing. In vitro evaluation of allergen-specific IgE may be utilized for confirmation of allergy. Predictive serum IgE levels for positive (failed) or negative (successful) oral food challenges for certain foods have been determined.

Management of anaphylaxis must focus on both acute events (to include possible biphasic reactions) as well as long term prevention of recurrence. While anaphylaxis accounts for a small number of ambulance dispatches and emergency department visits, prompt intervention remains important to positive outcomes. Expert panel recommendations confirm that treatment of anaphylaxis should include early administration of epinephrine. Regardless of the cause of anaphylaxis, the expert panel sponsored by the National Institute of Allergy and Infectious Diseases (NIAID) within the U.S. National Institutes of Health recommends that the cornerstone of management begin with the following concurrent steps: (i) elimination of additional allergen exposure, (ii) intramuscular injection of epinephrine, and (iii) call for help (activate the code team in the hospital or the emergency medical system in the community). This should not delay the administration of epinephrine if available. After these interventions adjuvant interventions should be considered.

Basophils

In humans, basophils are the least frequent of the three granulocytes, typically accounting for less than 0.5 percent of blood leukocytes. Basophils circulate as mature cells and can be recruited into tissues, particularly at sites of immunological or inflammatory responses, but they ordinarily do not reside in tissues.

Basophils express the high-affinity receptor for IgE (FceRI) on their surface, and both types of cells can be triggered to release potent mediators in response to activation via the FceRI, e.g., when their cell-bound IgE recognizes bi- or multivalent allergens. Accordingly, mast cells and basophils have long been regarded as important effector cells in asthma, hay fever, and other allergic disorders. Indeed, it is thought that the cells' cytoplasmic granule-associated preformed mediators, including histamine and certain proteases, their lipid mediators (such as prostaglandin D2 and leukotriene C4), which are generated upon activation of the cells, and their cytokines, contribute to many of the characteristic signs and symptoms of these diseases.

Because numbers of blood basophils can be very low even in apparently normal individuals it can be difficult to determine whether examples of basophilopenia reflect pathological processes as opposed to normal variation. Nevertheless, reduced numbers of circulating basophils have been reported in several disorders. Basophilopenia has been recorded in association with urticaria and anaphylaxis, but the extent to which this finding represents a loss of metachromatic staining of circulating degranulated cells rather than a true decrease in the number of cells is undetermined. Basophilopenia occurs in conditions that are also associated with eosinophilopenia; these conditions are often associated with increased secretion of adrenal glucocorticoids. Basophil counts may diminish, sometimes markedly, during leukocytosis accompanying infection, inflammatory states, immunological reactions, neoplasia, or hemorrhage. Also, basophil counts are diminished in thyrotoxicosis or after pharmacologic administration of thyroid hormones, and, conversely, basophil counts may be increased in myxedema or after ablation of thyroid function. A rapid and significant drop of up to 50 percent in blood basophil levels has been documented at ovulation. A few patients with an apparent total lack of basophils have been reported.

In contrast to the extensive studies on mast cells and eosinophils, the in vivo roles of basophils have been poorly studied and defined. This is partly to the lack of proper in vivo models to study basophils. See Matsuoka et al. PLOS ONE 2013, 8, (4) (Novel Basophil- or Eosinophil-Depleted Mouse Models for Functional Analyses of Allergic Inflammation).

Pramipexole has the formula (I)

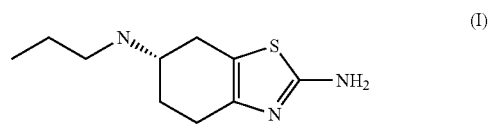

is a pharmaceutically active compound acting as a dopamine $D_2$ receptor agonist. It is indicated for treating early stage Parkinson's disease and restless legs syndrome (RLS), furthermore it is investigated for treating bipolar disorder, clinical depression and fibromyalgia.

Pramipexole is the (S)-enantiomer of $N^5$-propyl-4,5,6,7-tetrahydro-1,3-benzothiazole-2,6-diamine. The (R)-enantiomer thereof, dexpramipexole ((6R)-4,5,6,7-tetrahydro-N6-propyl-2,6 benzothiazole diamine), has been investigated for the treatment of amyotropic lateral sclerosis (ALS).

In the marketed medicaments, which are tablets for oral administration, pramipexole is present in the form of a dihydrochloride monohydrate salt. This salt is a crystalline compound, which is extremely well soluble in water.

Originally, pramipexole was sold (under brand names Mirapexin® or Sifrol®) as tablets with immediate release of the drug; the inactive ingredients are mannitol, maize starch, colloidal silica, povidone and magnesium stearate. The usual therapeutical dose is one tablet comprising from 0.125 to 1.5 mg of pramipexole dihydrochloride monohydrate three times a day. Subsequently, an extended release tablet has been developed and introduced into clinical practice (e.g. under the brand name Mirapex® ER or Sifrol® ER); such tablet comprising from 0.375 to 4.5 mg of pramipexole dihydrochloride is administered once-a-day. Pramipexole, dexpramipexole and related compounds and various formulations of such compounds are discussed in US 2007/0259930, 2009/0042956, 2009/0054504, 2011/0009460, 2011/0293718, 2011/0190356, 2011/0224268, 2012/

0225915, 2013/0230569, 2013/0123312, 2013/0245081, U.S. Pat. Nos. 8,524,695, 8,518,926, 8,519,148, 8,445,474, and 8,017,598.

A phase III study randomized 943 subjects in double-blind, placebo controlled trials to assess the safety and efficacy of dexpramipexole in treating ALS, as disclosed in a poster session at the international eosinophil society meeting 2013. Subjects were randomized to 150 mg dexpramipexole twice daily or placebo for up to 18 months. Monthly CBCs were obtained in both studies. Dexpramipexole was shown to reduce white blood cell counts, especially eosinophil and basophils (see FIGS. 1 to 4).

SUMMARY OF THE INVENTION

Briefly, the subject invention relates to methods for treating or relieving at least one symptom of an urticarial disorder, angioedema, and/or anaphylaxis in a mammal comprising: administering to the mammal, such as a human, a therapeutically effective amount of pramipexole and/or dexpramipexole or a pharmaceutically acceptable salt thereof. A compound such as a steroid, an antihistamine, a leukotriene receptor antagonist (LRTA), a nasal steroid, a nasal antihistamine, allergen immunotherapy, an oral antihistamine H1 and H2 blocker, and/or a proton pump inhibitor, can also be administered. The invention also relates to methods of treating or relieving at least one symptom of diseases including basophilia in a mammal comprising administering to the mammal a therapeutically effective amount of pramipexole and/or dexpramipexole or a pharmaceutically acceptable salt thereof. Such diseases include CML, ulcerative colitis, rheumatoid arthritis, and basophilic leukemia. In addition, the invention includes methods for treating or relieving at least one symptom of an urticarial disorder, angioedema, or anaphylaxis in a mammal comprising administering to the mammal an effective amount of a dopamine agonist which reduces basophil counts.

One embodiment of the invention relates to methods of treating or relieving at least one symptom of an urticarial disorder, angioedema, or anaphylaxis in a mammal. The method comprises administering to the mammal a therapeutically effective amount of pramipexole and/or dexpramipexole or a pharmaceutically acceptable salt thereof (i.e., pharmaceutically acceptable salt of pramipexole and/or dexpramipexole). The at least one symptom may be any symptoms described in this disclosure including, for example, skin rash, redness, itchy bumps, burning or stinging sensations, hives, dermal edema, wheal, angioedema. The symptoms may last, for example, more than 3 weeks, or more than 6 weeks. In a preferred embodiment, the mammal may be a human. The therapeutically effective amount may be placed in a pharmaceutically acceptable solution. The relieving at least one symptom stated anywhere in this disclosure may be any one or more symptoms listed in this disclosure.

The method of administration may be any method including oral administration. In addition, the administration may comprise administration of additional compounds such as a steroid, an antihistamine, a leukotriene receptor antagonist (LRTA), a nasal steroid, a nasal antihistamine, allergen immunotherapy, an oral antihistamine H1 and H2 blocker, and/or a proton pump inhibitor or a combination of the above.

The therapeutically effective amount may be from 50 mg to about 300 mg per day, or about 150 mg to about 300 mg per day, for example, for a mammal. The mammal may be a human such as a child or an adult between 30 to 100 Kg or 40 to 80 Kg or 50 to 70 kg in weight. In addition, the dosage may be adjusted for mammals that are heavier or lighter than the weight listed above proportionally to their weight. In some preferred embodiments, the effective amount may be more than 300 mg per day such as 400 mg, 500 mg, 600 mg, 700 mg or 1 g or more per day.

In a preferred embodiment, a single or multiple administration may be performed per day to reach the desired dosage. Administration, for example, may be twice a day, 3 times a day, or 4 times a day. As one example, administration may comprise administering about 150 mg two times per day, or, administering about 75 mg four times per day.

Another embodiment of the invention relates to a method of treating or relieving at least one symptom of a disease including basophilia in a mammal comprising administering to the mammal a therapeutically effective amount of pramipexole and/or dexpramipexole or a pharmaceutically acceptable salt thereof. In the method, the disease including basophilia may be selected from the group consisting of chronic myelogenous leukemia (CML), ulcerative colitis, rheumatoid arthritis, and a basophilic leukemia.

Another embodiment of the invention relates to a method for treating or relieving at least one symptom of an urticarial disorder, angioedema, or anaphylaxis in a mammal comprising: administering to the mammal an effective amount of a dopamine agonist which reduces basophil counts. The dopamine agonist may be selected from the group consisting of pramipexole and dexpramipexole or a combination.

Another embodiment of the invention relates to a composition comprising pramipexole and/or dexpramipexole and a compound selected from the group consisting of a leukotriene receptor antagonist (LRTA), a steroid, an antihistamine, an antihistamine H1 and H2 blocker, and a proton pump inhibitor or a combination thereof.

DETAILED DESCRIPTION OF THE INVENTION

The subject invention relates to methods for treating or relieving at least one symptom of urticarial disorders including chronic idiopathic urticaria, angioedema, and anaphylaxis, or a combination of these disorders in a mammal, including humans. The method comprises administering to the mammal a therapeutically effective amount of pramipexole or dexpramipexole ((6R)-4,5,6,7-tetrahydro-N6-propyl-2,6 benzothiazole-diamine), or pharmaceutically acceptable salts thereof.

Urticaria, Angioedema, and Anaphylaxis

Basophils are directly involved in the mechanism of chronic idiopathic urticaria. Hence a treatment modality that either decreases basophil numbers or function provides a good tool to treat this disorder.

Figure 1:
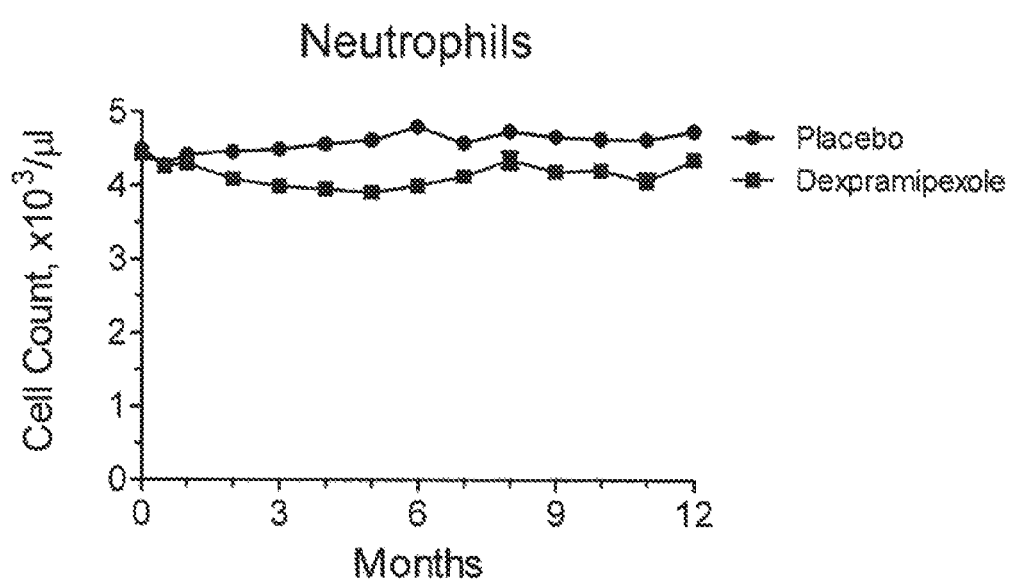
FIG. 1 is a graph of monthly neutrophil cell count after administering dexpramipexole that is shown in a prior art source.
Figure 2:
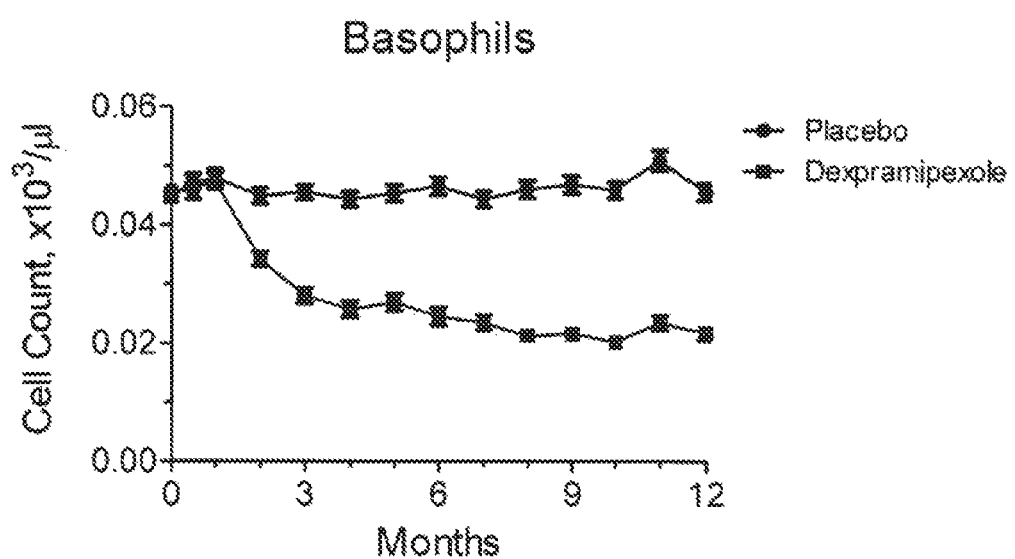
FIG. 2 is a graph of monthly basophil cell count after administering dexpramipexole that is shown in a prior art source.
Figure 3:
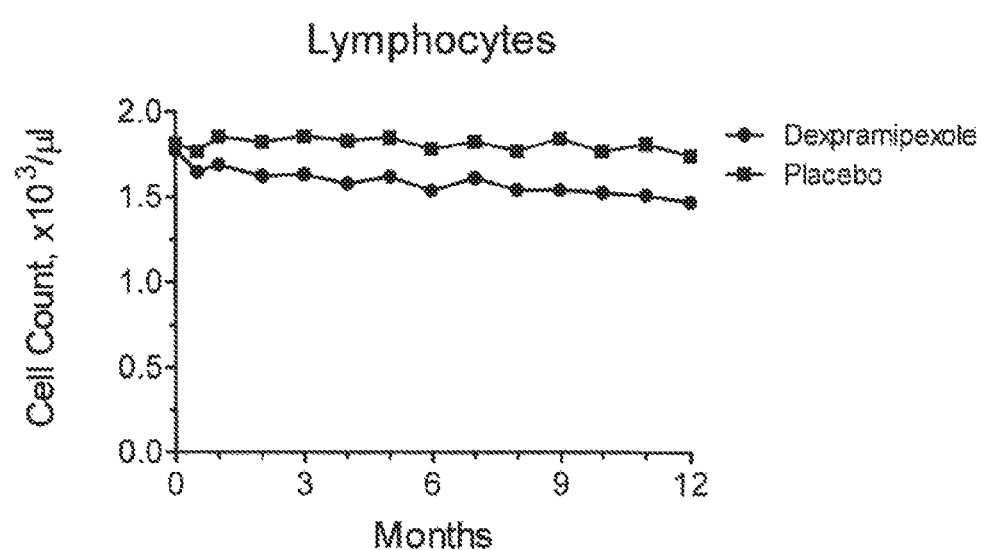
FIG. 3 is a graph of monthly lymphocite cell count after administering dexpramipexole that is shown in a prior art source.
Figure 4:
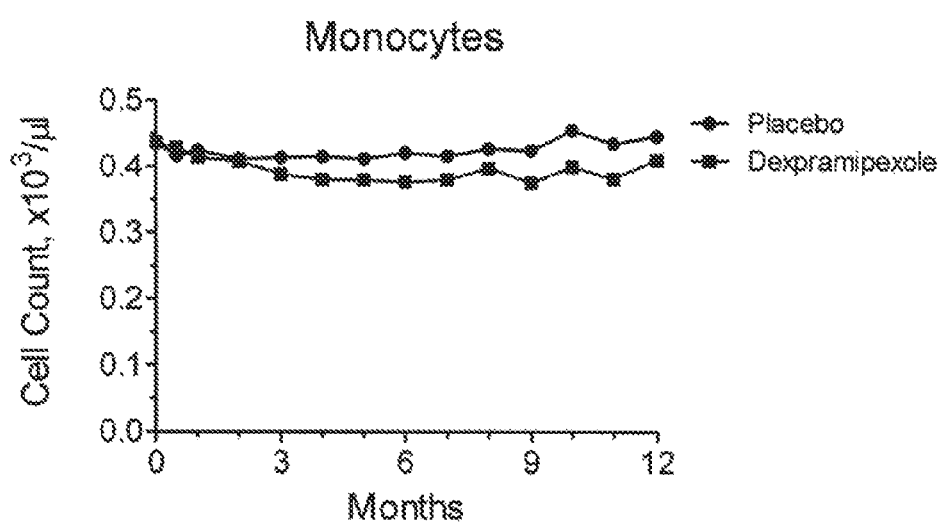
FIG. 4 is a graph of monthly monocyte cell count after administering dexpramipexole that is shown in a prior art source.
Figure 5:
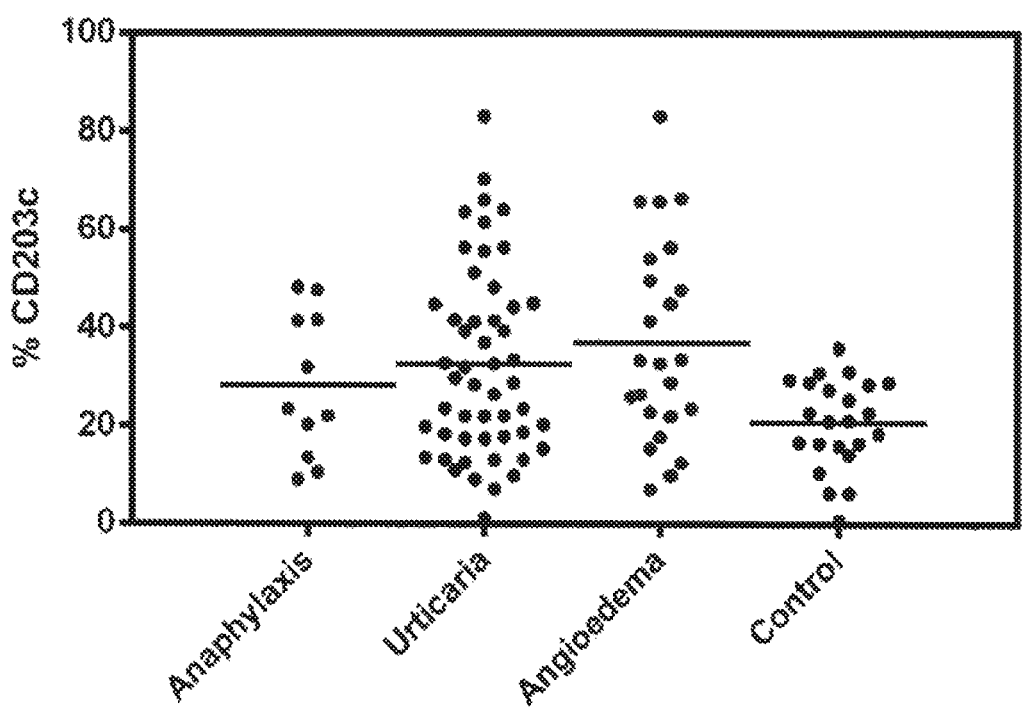
FIG. 5 is a graph of the expression of CD203c in anaphylaxis, urticaria, angioedema and control patients.

Applicant has shown that a much higher percentage of basophils from patients with chronic idiopathic urticaria express the surface activation marker CD203c whereas CD69 levels remain unaffected. Patients with such a high CD203c expression have more of a basophil involvement as a part of their disease process and benefit from a drug that targets basophils. A total of 11 anaphylaxis, 51 urticaria and 24 angioedema patients' peripheral blood was obtained. Whole blood was stained with CD123, HLA-DR. CD203c. Basophils were identified as CD123 positive HLA-DR negative cells. CD203c expression is shown as percent positive basophils (see FIG. 5 and tables below).

|  | Anaphylaxis | Urticaria | Angioedema | Control |
|---|---|---|---|---|
| Mean | 28.14 | 32.43 | 36.94 | 20.72 |
| Std. Deviation | 14.73 | 19.12 | 20.52 | 9.121 |
| Std. Error of Mean | 4.442 | 2.678 | 4.189 | 1.902 |

| Number of points | Anaphylaxis | Urticaria | Angioedema | Control |
|---|---|---|---|---|
| Analyzed | 11 | 51 | 24 | 23 |
| Outliers | 0 | 0 | 0 | 0 |

The present invention provides new and useful therapeutic methods for treatment of chronic idiopathic urticaria, angioedema or anaphylaxis, all of which are disorders involving basophil over-activation.

Dexpramixole ((6R)-4,5,6,7-tetrahydro-N6-propyl-2,6 benzothiazole diamine), decreases number of basophils in the circulation hence regardless of the activation status of these cells, will reduce disease activity. Reducing basophils also leads to a reduction in activated or un-activated basophils.

Disclosed herein are methods for treating or relieving at least one symptom of urticarial disorders, angioedema, or anaphylaxis in a mammal (e.g. human) with an effective amount of dexpramipexole or related compounds, either acutely or prophylactically. As used herein, a "therapeutically effective amount" is that amount which reduces or eliminates symptoms of the above note disorders. The reduction in basophil levels observed with dexpramipexole therapy results in remission of urticarial, angioedema, or anaphylaxis symptoms.

Basophils play a critical role in allergic disorders such as chronic idiopathic urticaria, idiopathic angioedema, anaphylaxis and a combination of these disorders, such as urticarial and anaphylaxis, or urticaria and angioedema. Basophils also play an important role in allergic disorders such as asthma and allergic rhinitis. In one embodiment, the methods of the invention are used to treat the above disorders where basophil activation marker CD203c>20%, 30% or 40%.

Conditions associated with increased numbers of blood basophils (basophilia) can be categorized as below:

Inflammatory/Immunological Responses

An increase in the number of basophils is commonly associated with hypersensitivity disorders of the IgE-associated "immediate" type. This is often accompanied by increased levels of IgE. While serum IgE levels and basophil numbers are not directly related, increased levels of IgE are associated with increased expression of FceRI on the surfaces of both basophils and mast cells. Moreover, basophils can be recruited into tissues at sites of IgE-associated and other immunological responses. Basophil levels can be elevated in ulcerative colitis and rheumatoid arthritis, whereas many inflammatory conditions that cause a leukocytosis are associated with basophilopenia. Basophilia can also occur in subjects exposed to ionizing radiation. The compositions of the subject invention are useful in treating or relieving at least one symptom of these disorders.

Hematopoietic Stem Cell Diseases

Chronic Myeloproliferative Diseases (CML). The concentration of blood basophils is slightly increased in many patients with polycythemia vera, idiopathic myelofibrosis, and thrombocythemia, and a slight increase in the absolute basophil count can be a useful early sign of a myeloproliferative disease. An increase in absolute basophil count occurs in virtually all patients with CML, and, in some, basophils can represent 20 to 90 percent of blood leukocytes. Exaggerated basophilia of this type is a poor prognostic sign and can herald transformation to the accelerated phase of CML. The basophil in myeloproliferative diseases is generally thought to be derived from the malignant clone, and in CML can contain the Ph chromosome and presumably also the breakpoint cluster gene rearrangement on chromosome 22. The basophils in CML exhibit a variety of ultrastructural and biochemical abnormalities, in some cases obscuring some of the typical distinctions between basophils and mast cells. Release of basophil-associated histamine can lead to episodes of flushing, pruritus, and hypotension in occasional patients with basophilic CML, and severe peptic ulcer of the stomach and duodenum can occur in association with hyper-secretion of gastric acid and pepsin. Ph chromosome-positive acute basophilic leukemia may be a presenting manifestation of CML. The compositions of the subject invention are useful in treating or relieving at least one symptom of these disorders.

Basophilic Leukemias

The literature includes many reports of basophilic leukemias. However, the basis for designating some cases as basophilic leukemias as opposed to examples of myelogenous leukemia with an associated pronounced basophilia is not always clear. Accordingly, these conditions are referred to herein as leukemias associated with basophilia. In addition to extreme basophilia in chronic phase CML, or as a manifestation of the accelerated phase of CML, acute basophilic leukemia apparently can rarely occur de novo. A form of acute myelogenous leukemia (AML) in which the blast cells contain a translocation between chromosomes 6 and 9, t(6;9), is associated with marrow basophilia, although basophilia can also occur in cases of AML with other translocations or inversions. Finally, basophilic maturation of leukemic cells can be observed in cases of acute promyelocytic leukemia.

While the clinical and pathological features of acute basophilic leukemia are largely similar to those of myelogenous leukemia, affected patients occasionally exhibit symptoms that result from release of mediators (especially histamine) derived from degranulating or dying basophils. Remission induction therapy is similar to that used for other types of AML, but management can be complicated by shock due to massive release of histamine and other mediators associated with acute cytolysis. The compositions of the subject invention are also useful in treating or relieving at least one symptom of these disorders.

Concomitant therapy for the above disorders can include a leukotriene receptor antagonist (LRTA), e.g. montelukast or Singulair, nasal steroids or nasal antihistamines, allergen immunotherapy, oral antihistamines H1 and H2 blockers, and proton pump inhibitors.

Compounds and Compositions of the Invention

The invention is directed to pharmaceutical compositions including an effective amount of pramipexole and dexpramipexole ((6R)-4,5,6,7-tetrahydro-N6-propyl-2,6 benzothiazole diamine). These compounds, related compounds, various formulations and dosages, and modes of administration of such compounds and compositions are discussed in US Published Applications 2007/0259930, 2009/0042956, 2009/0054504, 2011/0009460, 2011/0293718, 2011/0190356, 2011/0224268, 2012/0225915, 2013/0230569, 2013/0123312, 2013/0245081, U.S. Pat. Nos. 8,524,695, 8,518,926, 8,519,148, 8,445,474, and 8,017,598 each of which is hereby incorporated by reference in its entirety.

At least about 150 mg of dexpramipexole per day are typically administered to a patient in need of treatment, or, at least about 300 mg of dexpramipexole, or at least about 600 mg of dexpramipexole are administered to a patient in need of treatment per day. Such administration can be carried out as a single dose once per day, or in certain embodiments, two or more doses of dexpramipexole can be administered two or more times per day. Therefore, the pharmaceutical compositions of the invention include 50 mg of dexpramipexole and a pharmaceutically acceptable excipient, and in some embodiments, such pharmaceutical compositions can include at least 75 mg, 100 mg, 125 mg, 150 mg, 300 mg, 400 mg, 450 mg, 500 mg, or at least 600 mg of dexpramipexole and one or more pharmaceutically acceptable excipients.

In various embodiments, dexpramipexole administered or incorporated into the pharmaceutical compositions can be enantiomerically pure or enantiomerically enriched to such an extent that the effects of residual (6S)-2-amino-4,5,6,7-tetrahydro-6-(propylamino)benzothiazole (pramipexole) is either absent or sufficiently small to allow for high dosage administration of dexpramipexole relative to enantiomerically pure or enantiomerically enriched pramipexole. A description of methods for producing high purity dexpramipexole can be found in U.S. application Ser. No. 12/049,235, which is hereby incorporated by reference in its entirety.

Treatment with dexpramipexole includes administering daily doses of about 100 mg or more, about 125 mg or more, about 150 mg or more, 300 mg or more, 400 mg or more, 450 mg or more, 500 mg or more, or 600 mg or more without the adverse side effects.

Moreover, because dexpramipexole is well tolerated, in some embodiments, treatment including administration of daily doses of about 100 mg or more, about 125 mg or more, about 150 mg or more, or about 300 mg or more, or about 400 mg or more, or about 450 mg or more, or about 500 mg or more, or about 550 mg or more, or about 600 mg or more of dexpramipexole can be carried out for prolonged periods of time such as, for example, 12 weeks or more, 6 months or more, 1 year or more and, in certain embodiments, for 2, 3, 5 or 10 years or more, and in other embodiments, for an indefinite period of time. Accordingly, embodiments of the invention include methods of treating or relieving at least one symptom of urticarial disorders, angioedema and anaphylaxis or a combination of these disorders, by administering dexpramipexole for an extended or prolonged period of time. In some embodiments, the extended period of time may be about 12 weeks or longer, about 6 months or longer, about 1 year or longer. In other embodiments, a method of treating or relieving at least one symptom of urticarial, anaphylaxis or angioedema or a combination of these disorders comprises administering dexpramipexole on a maintenance dosing regimen. In such embodiments, the maintenance dosing regimen can include administering about 100 mg or more, about 125 mg or more, about 150 mg or more, about 300 mg or more, about 450 mg or more, about 500 mg or more, or about 550 mg or more, or about 600 mg or more of dexpramipexole per day without any titration (or an initial dosing regimen of less than the maintenance dose). Thus, various embodiments are directed to maintenance therapy in which a dosing schedule for dexpramipexole is maintained for an extended period of time without titration or otherwise changing the dosing schedule. In such embodiments, the extended period of time can be about 12 weeks or longer, about 6 months or longer, about 1 year or longer, 2, 3, 4, 5, or 10 years or longer, and in certain embodiments, an indefinite period of time. In other embodiments, the maintenance dosing may include administering less than the initial daily dose, such as, less than about 150 mg, or less than about 300 mg, or less than about 600 mg of dexpramipexole per day.

Other embodiments of the invention includes the use of other dopamine receptor agonists that reduce basophil counts, in the treatment of the disorders discussed above.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

All references, patents and patent applications cited in this document is hereby incorporated by reference in its entirety.

We claim:

1. A method for treating anaphylaxis in a mammal comprising: administering to the mammal a therapeutically effective amount of dexpramipexole or a pharmaceutically acceptable salt thereof, wherein the mammal is characterized as having a basophil population with greater than 20% CD203c positive basophil.

2. The method of claim 1, wherein the CD203c positive basophil of the basophil population is greater than 30%.

3. The method of claim 1, wherein the CD203c positive basophil of the basophil population is greater than 40%.

4. The method of claim 1, further comprising identifying the mammal as having a basophil population with greater than 20% CD203c positive basophil.

5. The method as in claim 1, wherein the administration is orally.

6. The method as in claim 1, wherein the mammal is a human.

7. The method as in claim 1, wherein the method further comprises administration of a leukotriene receptor antagonist (LRTA), a nasal steroid, a nasal antihistamine, allergen immunotherapy, an oral antihistamine H1 and H2 blocker, and/or a proton pump inhibitor.

8. The method as in claim 1, wherein the therapeutically effective amount is from about 50 mg to about 300 mg per day.

9. The method of claim 1, wherein the therapeutically effective amount is from about 150 mg to about 300 mg per day.

10. The method of claim 1, wherein the therapeutically effective amount is about 300 mg or more per day.

11. The method of claim 1, wherein administering comprises administering a dose equal to about half of a daily dose two times per day.

12. The method of claim 1, wherein administering comprises administering a dose equal to about one quarter of a daily dose four times per day.

13. The method of claim 1, wherein administering comprises administering about 150 mg two times per day.

14. The method of claim 1, wherein administering comprises administering about 75 mg four times per day.

15. The method of claim 4, wherein the basophil population is identified as CD123 positive HLA-DR negative cells.

16. The method of claim 1, wherein the anaphylaxis is a food-induced anaphylaxis, an exercise-induced anaphylaxis, an idiopathic anaphylaxis, or a combination thereof.

\* \* \* \* \*